United States Patent [19]

Wakatake

[11] Patent Number: 4,919,887

[45] Date of Patent: Apr. 24, 1990

[54] AUTOMATIC ANALYZER

[75] Inventor: Koichi Wakatake, Koganei, Japan

[73] Assignee: Nittec Co., Ltd., Tokyo, Japan

[21] Appl. No.: 184,637

[22] PCT Filed: Sep. 16, 1987

[86] PCT No.: PCT/JP87/00679

§ 371 Date: Apr. 20, 1988

§ 102(e) Date: Apr. 20, 1988

[87] PCT Pub. No.: WO88/02120

PCT Pub. Date: Mar. 24, 1988

[30] Foreign Application Priority Data

| Sep. 16, 1986 | [JP] | Japan | 61-216011 |
| Sep. 19, 1986 | [JP] | Japan | 61-219174 |
| Oct. 3, 1986 | [JP] | Japan | 61-234295 |
| Jan. 19, 1987 | [JP] | Japan | 62-8112 |
| Feb. 12, 1987 | [JP] | Japan | 62-17750 |

[51] Int. Cl.$^5$ .................................................. G01N 35/00
[52] U.S. Cl. ........................................ 422/67; 422/63; 422/64; 436/43
[58] Field of Search ................... 422/63, 64, 65, 66, 422/67; 235/375, 376, 492

[56] References Cited

U.S. PATENT DOCUMENTS

| Re. 31,150 | 2/1983 | Ginsberg et al. | 422/64 |
| 3,660,638 | 5/1972 | Oberli | 235/61.6 R |
| 3,703,336 | 11/1972 | Rosse et al. | 356/39 |
| 3,796,544 | 3/1974 | Zauft et al. | 422/66 |
| 4,061,469 | 12/1977 | DuBose | 422/64 |
| 4,115,861 | 9/1978 | Allington | 364/497 |
| 4,169,125 | 9/1979 | Rodriguez et al. | 422/65 |
| 4,654,512 | 3/1987 | Gardosi | 235/376 |
| 4,672,182 | 6/1987 | Hirokawa | 235/436 |
| 4,701,600 | 10/1987 | Beech et al. | 235/375 |

FOREIGN PATENT DOCUMENTS 117386  6/1985  Japan .

Primary Examiner—Michael S. Marcus
Assistant Examiner—D. John Griffith, Jr.
Attorney, Agent, or Firm—Wenderoth, Lind & Ponack

[57] ABSTRACT

The automatic analyzer relating to the invention is characterized in that since drive and control of the automatic analyzer and storage of the measuring data are realizable on the IC card, operability of such kind of automatic analyzer is sharply simplified, the system can be miniaturized substantially to a low cost, moreover, in case the automatic analyzer gets damaged, portion and cause of the damage can be found easily and quickly.

3 Claims, 11 Drawing Sheets

AUTOMATIC ANALYZER

TECHNICAL FIELD

This invention relates to an automatic analyzer operating automatically for biochemical analysis and immunological analysis.

BACKGROUND OF THE INVENTION

Various kinds of automatic analyzers have been proposed. However, many of the recent automatic analyzers are rather complicated, large-sized, high-cost and high-speed operating, and moreover, involve an exceedingly complicated operation, and therefore a specialized operator must be attendant thereon all the time, and personnel expenses are a problem.

This kind of large-sized automatic analyzer is not always required by local hospitals and clinics where a large amount of blood examination is not necessary, and in such circumstances a specialized examination center is requested to carry out blood examination of respective patients.

Consequently, where an urgent examination is required, an inconvenience may result in such local hospitals and clinics, a waste of money is quite unavoidable, and moreover, in case work for comparing an analysis with the patient's blood or reexamination is required, a long time will be needed for obtaining a result.

This invention has been made in view of the situation described above, and its object is to provide a simple automatic analyzer, miniaturized to cope with a need by local hospitals and clinics, which is very simple in operation and construction, and moderate in cost.

DISCLOSURE OF THE INVENTION

In order to attain the aforementioned object, the automatic analyzer relating to the invention comprises a means for moving a plurality of samples to a sample sucking position, a means for sucking a predetermined quantity of sample at the sample sucking position and pouring the predetermined quantity into a reaction cell, a means for moving the reaction cell to an optical measuring position, a means for pouring a reagent corresponding to a charactristic to be measured into the reaction cell, a means for moving a reagent container in which the reagent corresponding to a characteristic to be measured is contained to a reagent sucking position, a means for measuring a sample in the reaction cell optically, a means for washing the reaction cell after completion of the measurement, an IC card storing various starting command signals and measurement data, a reader/writer for reading command signals of the IC card and writing the measurement data.

In the invention, the IC card comprises a starting IC card in which command signals for actuating and controlling a sample moving means, a sampling means, a reaction cell moving means, a reagent pouring means, an optical measuring means and washing means are inputted, and a memory IC card storing data measured by the optical measuring means. Needless to say, a single IC card may be so constructed as to work for both starting and memory at the same time.

In the invention, a thermostat is provided having a plurality of heating members at predetermined intervals on the bottom of a thermostatic oven constituted by a heating medium, and the temperature in the thermostatic oven is made uniform by controlling the heating members separately by a temperature controller.

Further, in the invention, a table holding the reaction cells thereon turn in steps the number of which is one less than the number of the reaction cells held on the table so that the reaction cells will be moved relative to a fixed point one by one intermittently counter to the direction in which the table turns.

BEST MODE FOR CARRYING OUT THE INVENTION

Figure 1:
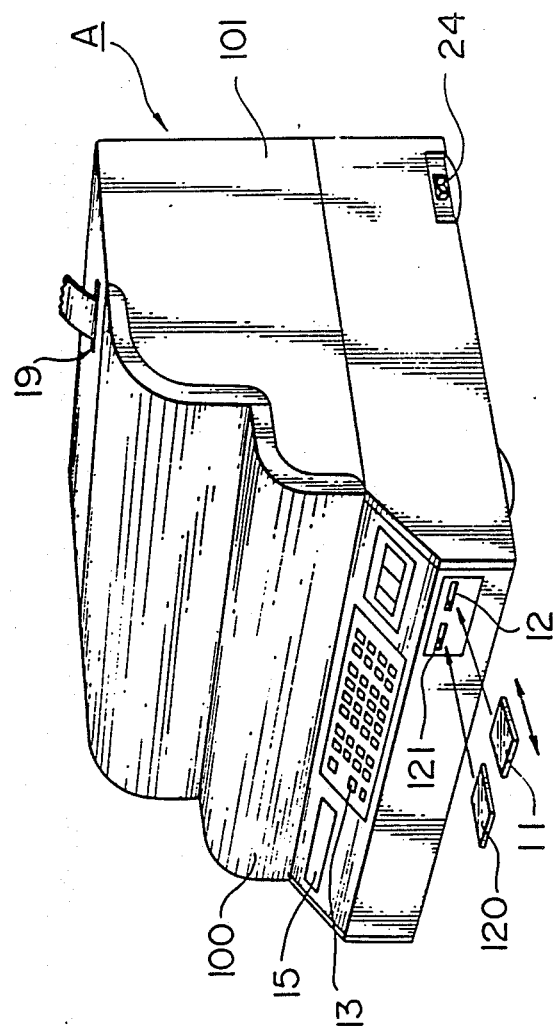
FIG. 1 is a perspective view showing a general construction of an automatic analyzer according to one embodiment of the invention.

The invention will now be described in detail with reference to the accompanying drawings representing one preferred embodiment thereof.

As shown in FIGS. 1–4 and FIG. 12, a simple automatic analyzer A according to the invention comprises roughly an analyzing portion V and a controlling portion W.

The analyzing portion V comprises a reaction cell moving device for moving a reaction cell 1 at predetermined timed intervals to a sample (serum) pouring position a, a first reagent pouring position b, a second reagent pouring/stirring position c, an optical measuring position d and washing positions $e_1$ to $e_4$, a sample container 2 in which a sample to be measured is contained in a quantity as required, a sample container moving device (not shown) for moving the sample container 2 linearly to a sample sucking position f, a sampling pipette means 3 for sucking up a necessary quantity of sample from the sample container 2 and pouring it into the reaction cell 1, a first reagent pipette means 4 for pouring a first reagent corresponding to the characteristic to be measured into the reaction cell 1, a second reagent pipette 5 for pouring a second reagent corresponding to the characteristic to be measured into the reaction cell 1, a stirring device (not shown) interlocking with the second reagent pipette means 5, an optical measuring device 7, a washing device 8, a reagent moving device 10 for moving reagent container 9 having cells in which the first and second reagents are contained to a first reagent sucking position g and a second reagent sucking position h.

On the other hand, the controlling portion W comprises a CPU for controlling the drive of the aforementioned devices corresponding to the characteristics to be measured, an operation IC card 11 ready for reading and writing, a reader/writer 12 in which the operation IC card 11 is installed, a switch assembly 13 for selecting the analyzing characteristics of a respective sample, a sequential No. and a specified sample No. or sequential No., a display unit 15, a start switch 16, a stop switch 17, a reset switch 18, a memory IC card 120 for storing information and for reading thereinto and writing out therefrom data obtained by the optical measuring device 7, a reader/writer 121 in which the memory IC card 120 is installed, a printer 19 for printing out measured results and so forth. Reference numeral 100 in the drawings denotes a double closing cover mounted rotatably on a case body 101, reference numeral 20 in FIG. 3 denotes a sampling pump, 21 denotes a first reagent pump, 22 denotes a second reagent pump, 23 denotes a washing pump, and 24 in FIG. 4 denotes a main switch.

The reaction cell moving device B moves a plurality (36 in number) of reaction cells 1 held on a reaction cell table (not shown) intermittently one pitch at a time and successively to required positions for heating up to almost biological temperature (37° C.) under the control of a thermostatically controlled heater 60 described hereinafter. The reaction cells 1 move counterclockwise in FIG. 2 through a number of positions one less than the number of cells, thus moving the reaction cells 1 one by one intermittently in the opposite direction, i.e. clockwise in FIG. 2. A well-known pulse motor is used as the reaction cell moving means.

The sample containers 2 are held in a sample cassette 30 in two rows of 10 or 20 containers all told, and the sample cassette 30 is moved so as to move the axial centers of the containers in succession and intermittently, to the sample sucking position f on the path of swinging movement of the sampling pipette means 3.

The sample cassette 30 holding the sample containers 2 therein is moved by the sample container moving device consisting of a cross feed means.

As in the case of a well-known sampling pipette, the sampling pipette means 3 comprises an arm 32 with its one end journaled on a shaft 31, a pipette 33 disposed on the other end of the arm 32, a sampling pump 20 connected to the pipette 33 for sucking up the required quantity of a sample and to discharge it to the reaction cells 1, a driving device (not shown) for turning the arm 32 from the sample sucking position to the sample discharging position a and further to a washing position i with a predetermined timing and then lifting it at each position.

The sample measuring system operates by filling a suction system with water, sucking in the sample for measurement while isolating it from the water by a volume of air, then discharging the sample, and washing the inside of the pipette 33 with washing water led therethrough. For such washing, the pipette 33 is set at the pipette washing position i, and hence any remainder of the sample sticking on the surface of the pipette 33 is washed down at the position i.

Figure 5:
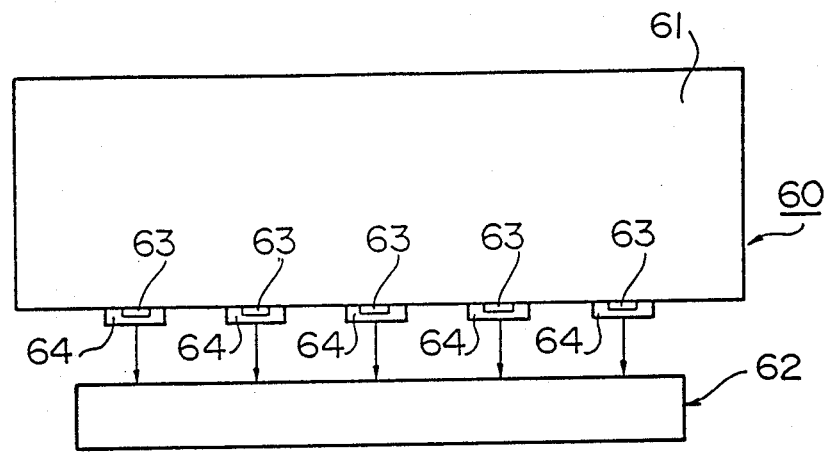
FIG. 5 is an explanatory drawing showing a schematic construction of a thermostat.

The thermostatically controlled heater 60 comprises, as shown in FIG. 5, a heating medium 61 mounted on an oven (not shown) in which a lower portion of the reaction cells 1 soak, and a constant temperature controller 62 disposed on the heating medium 61.

Figure 6:
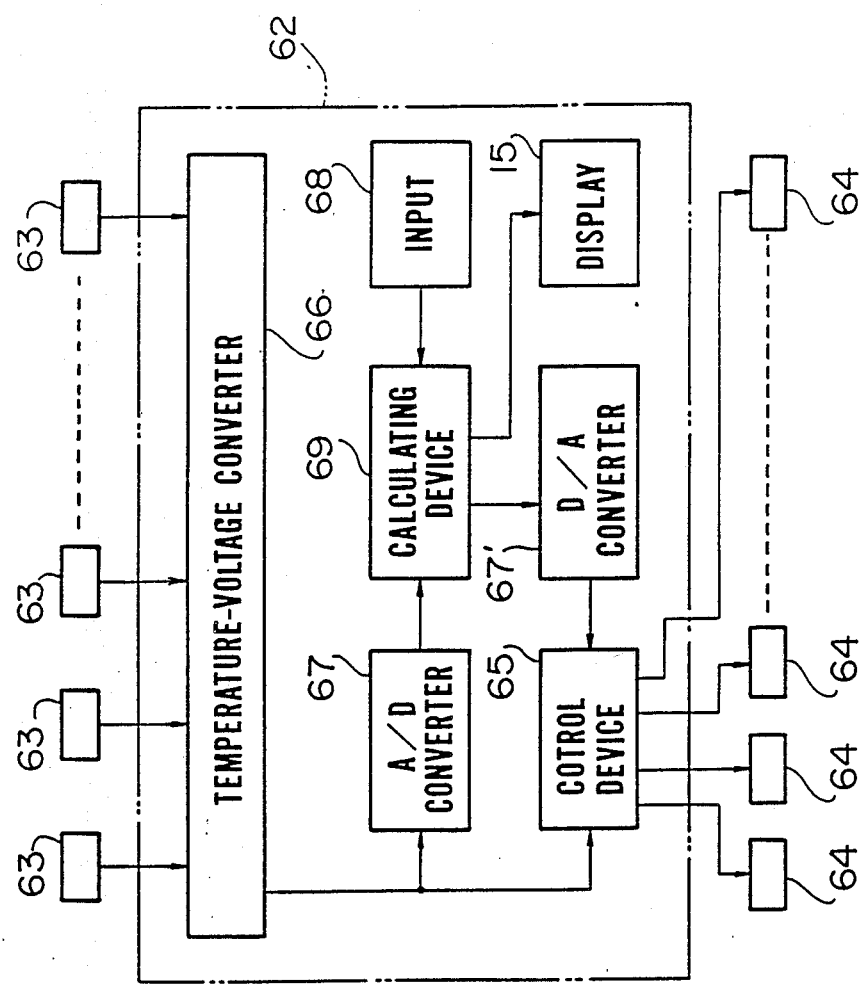
FIG. 6 is a block diagram showing a construction of a heat regulating unit.

The constant temperature controller 62 comprises, as shown in FIG. 6, a plurality of temperature detecting elements 63 for detecting temperature at each position of the heating medium 61, a plurality of heating elements 64, a temperature control device 65 for controlling the heating elements 64 according to temperature information obtained through the temperature detecting elements 63.

Each temperature detecting element 63 is constituted of a thermistor or the like and a plurality are mounted on a bottom portion of the heating medium separately at predetermined intervals.

The temperature information obtained through each temperature detecting element 63 as a variation of its resistance value is converted into voltage by a temperature-voltage converter 66, and an output from the temperature-voltage converter 66 is inputted to the temperature control device 65 for controlling voltage and current to the heating elements 64. Further, the temperature-voltage converter 66 has its output voltage converted into a digital value by an A/D converter 67, an output from the A/D converter 67 and an output from an input device 68 are processed by an arithmetic operation processing circuit, i.e. a calculator, 69, and the result thus obtained is converted into an analogue value by a D/A converter 67' and inputted to the temperature control device 65.

The aforementioned heating elements 64 are each constituted by a heater producing heat generated by a resistance wire. Further, the temperature control device 65 operates for unifying temperature at each heater mounting position of the heating medium 61 by subjecting each heating element 64 to on/off control according to information from the corresponding temperature detecting element 63.

Therefore, when temperature information corresponding to a set temperature is inputted to the input device 68, the output from the input device 68 is inputted to the aforementioned arithmetic operation processing unit 69, and a corresponding resistance value (for generating a heating power necessary for liquid to be heated and retained at 37° C.) in each temperature detecting element 63 is obtained according to a predetermined arithmetic expression. On the other hand, a change in resistance value of each temperature detecting element 63 is converted into voltage by the temperature-voltage converter 66, converted further into a digital signal by the A/D converter 67, and the digital value is inputted to the arithmetic operation processing unit 69. The arithmetic operation processing unit 69 operates for the aforementioned arithmetic processing according to a conversion coefficient determined by the temperature-voltage converter 66, the result of the operation is output to the D/A converter 67', and the D/A converter 67' generates a comparison voltage. That is, the processing unit 69 compares the output voltage from the temperature-voltage converter 66 through converter 67 with the voltage of the input 68 generating the aforementioned comparison voltage to the D/A converter 67', the temperature control device 65 controls voltage and current to each temperature detecting element 63 according to the comparison information and the sensed temperature from elements 63 to heat to the desired temperature, thus heating the liquid in the oven uniformly.

By constructing the heater 60 as described, the temperature distribution in the heater is easily made uniform, and a chemical reaction of the sample with the reagent can be equalized.

Figure 2:
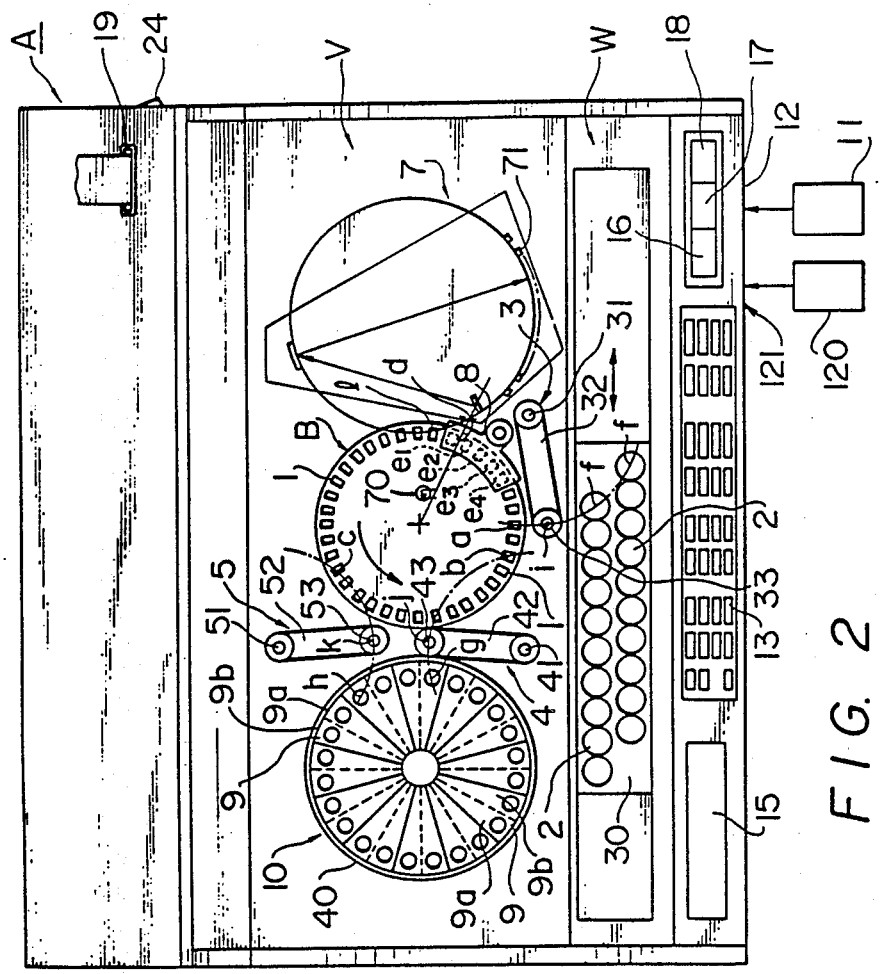
FIG. 2 is a plan view showing the construction of the automatic analyzer schematically.
Figure 3:
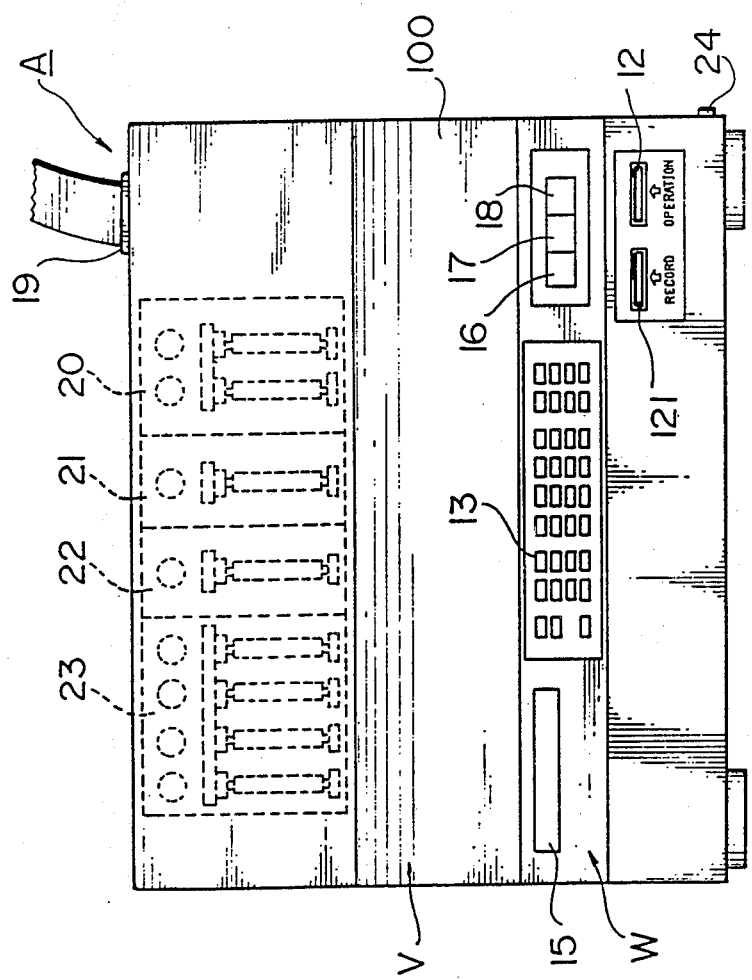
FIG. 3 is a front view of the automatic analyzer.
Figure 4:
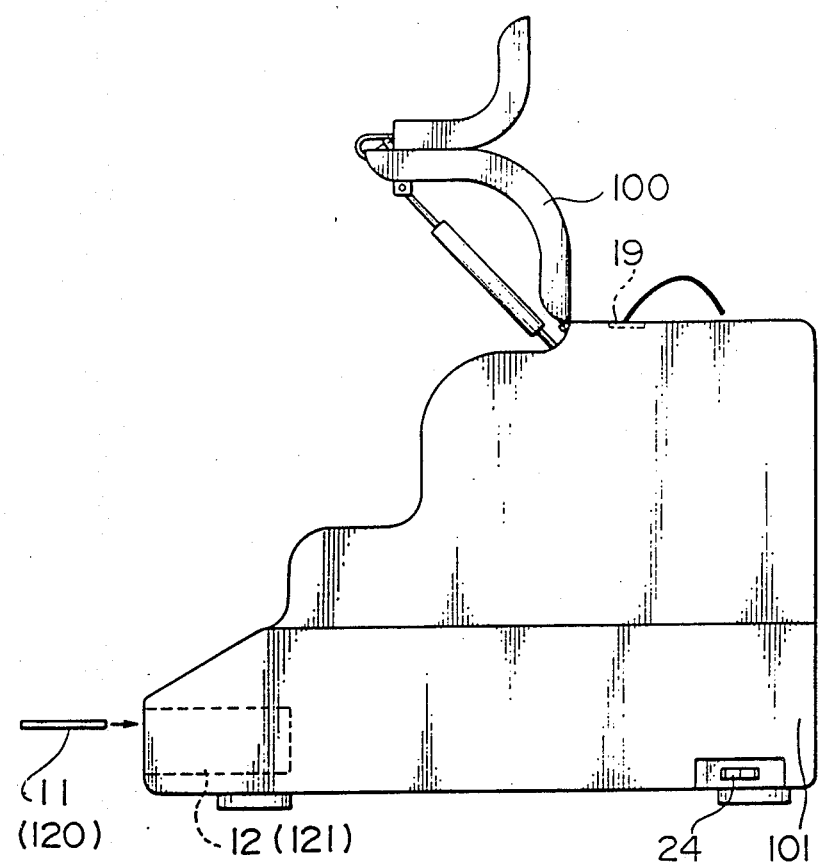
FIG. 4 is a right side view of the automatic analyzer.
Figure 7:
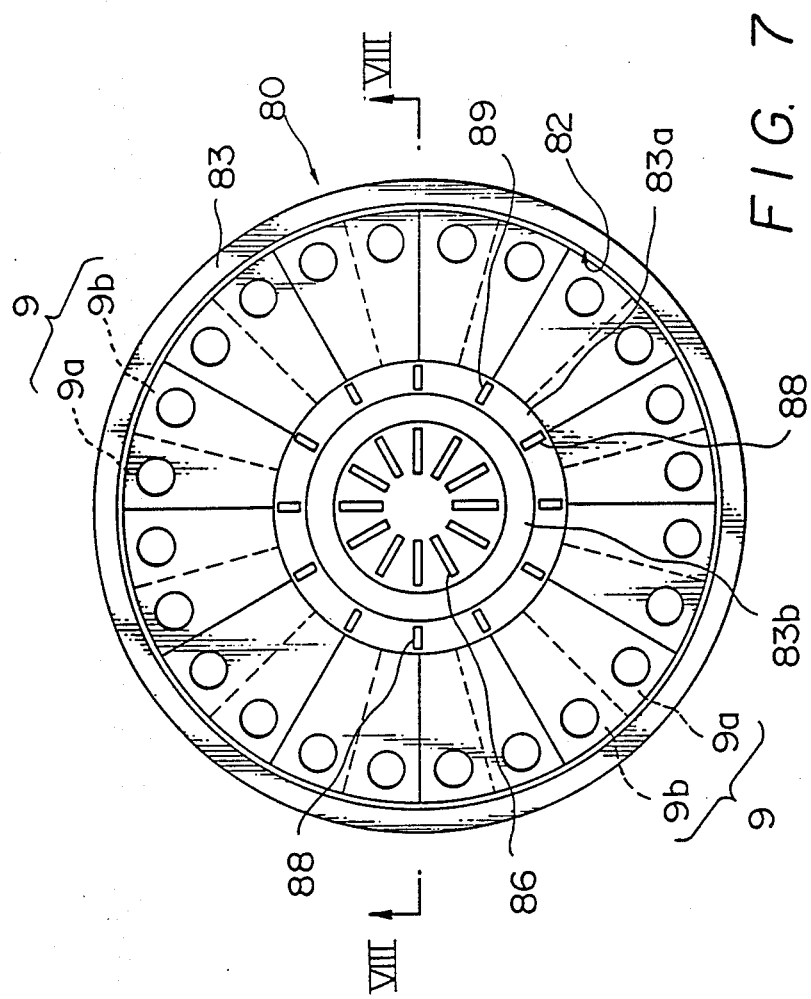
FIG. 7 is a plan view of a liquid cooling device.

The reagent moving device 10 comprises, as shown in FIGS. 2 and 7, the reagent containers 9 each having a cell 9a in which the first reagent is contained and further cell 9b in which a second reagent is contained, a container moving device (not shown) turning and controlling a table 40 on which the reagent containers 9 are placed and moving a reagent corresponding to the item being measured to the first reagent sucking position g or the second reagent sucking position h, the first reagent pipette 4 for sucking the first reagent as required in quantity from inside the cell 9a at the first reagent sucking position g, the second reagent pipette 5 for sucking the second reagent as required in quantity from inside the cell 9b at the second reagent sucking position h. The reagent containers 9 disposed on the table 40 are set at predetermined positions, and the positions are stored in the CPU. Further, there are a set of 12 reagent containers 9, and when the characteristic to be measured changes, one set can be replaced with another set. The reagents in the reagent containers 9 are cooled down to 10°-12° C. in a liquid cooling device 80.

The liquid cooling device 80 comprises, as shown in FIGS. 7-10, a heat insulating case 83 circular in plan view which is provided with a plurality of chambers 82 for containing the reagent containers 9 radially therein, a cover 84 installed detachably on an upward opening of the heat insulating case 83, an electronic cooling unit 85 disposed in a center cylindrical part 83a of the heat insulating case 83, and a fan 86 for forcedly blowing heat generated in the electronic cooling unit 85 out of the unit.

Figure 8:
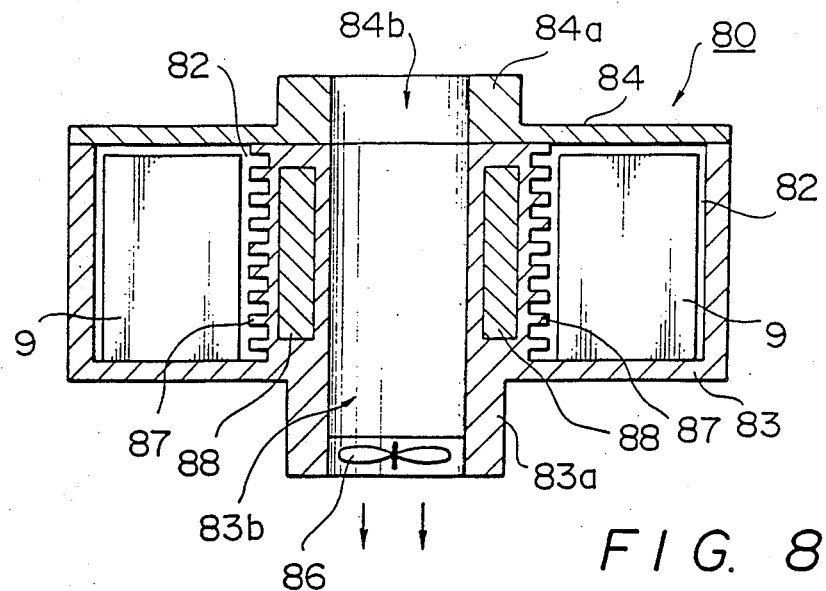
FIG. 8 is a sectional view taken on line VIII—VIII of FIG. 7.

The heat insulating case 83 is constituted by a heat insulating material, and comb-toothed radiation fins 87 are formed on the chamber side of the center cylindrical part 83a as shown in FIG. 8.

As in the case of the aforementioned heat insulating case 83, the cover 84 is circular in plan, an opening 84b communicating with a central space 83b of the heat insulating case 83 is formed at the central portion thereof, and a peripheral wall portion 84a of the opening 84b projects upward to form a grip. A plurality of openings (not shown) communicating with holes (not shown) for sucking liquid in the reagent containers 9 contained in the heat insulating case 3 are provided in the cover 84 at positions corresponding thereto.

Figure 9:
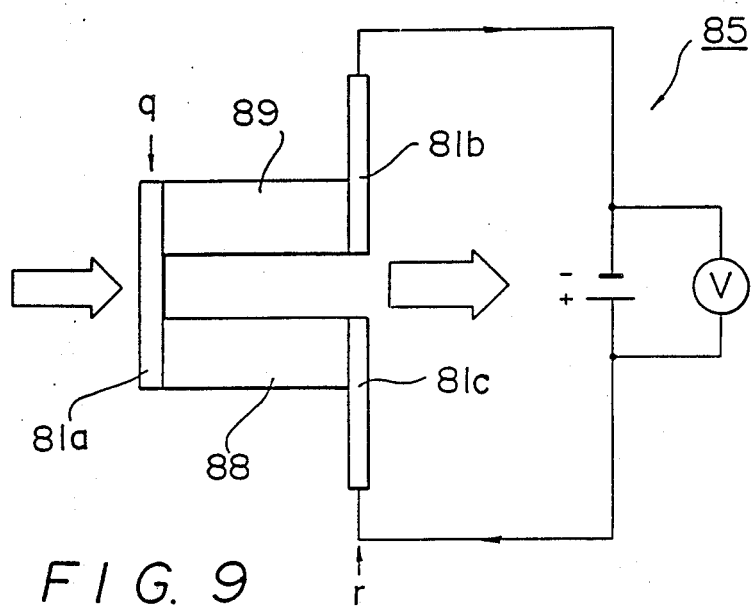
FIG. 9 is a schematic block diagram of an electronic cooling unit.

The electronic cooling unit 85 is constructed fundamentally, as shown in FIG. 9, of an N-type semiconductor 88 and a P-type semiconductor 89 formed of two different materials joined together through metals 81a, 81b, 81c, and when DC current is carried from a supply, for example, in the direction indicated by an arrow in FIG. 9, a junction q with the metal 81a becomes cool according to an endothermic effect, and a junction r with the metals 81b, 81c becomes hot according to a heating effect, thus producing the Peltier effect.

Figure 10:
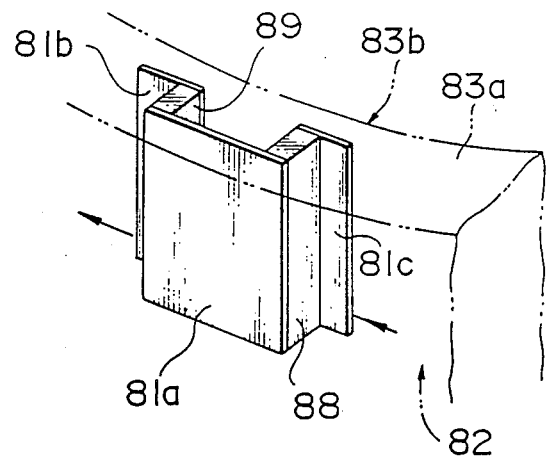
FIG. 10 is a fragmentary enlarged view showing an example of an array of an N type semiconductor and a P type semiconductor.

Accordingly, as shown in FIG. 10, the N-type semiconductor 88 and the P-type semiconductor 89 are arrayed alternately in the circumferential direction of the center cylindrical part 83a, the chamber sides of the pair of N-type semiconductor 88 and P-type semiconductor 89 are connected by the metal 81a, and the metals 81b, 81c are each connected in DC current flow connection to the center space side of the N-type semiconductor 88 and the P-type semiconductor 89, thereby producing a low-temperature region on the chamber side through an endothermic effect and a high-temperature region on the center space side.

Figure 11:
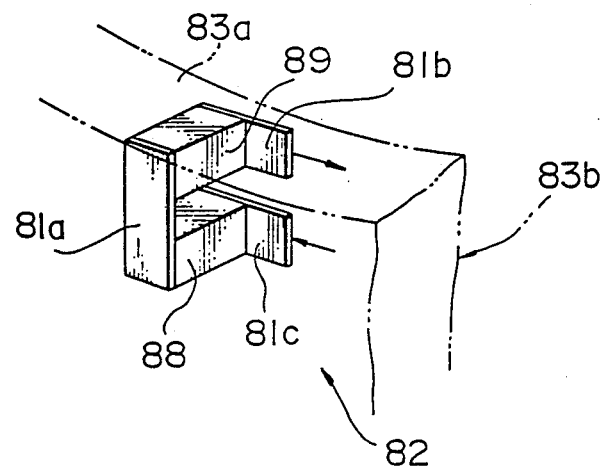
FIG. 11 is a fragmentary enlarged view showing another example of an array of an N type semiconductor and a P type semiconductor.
Figure 12:
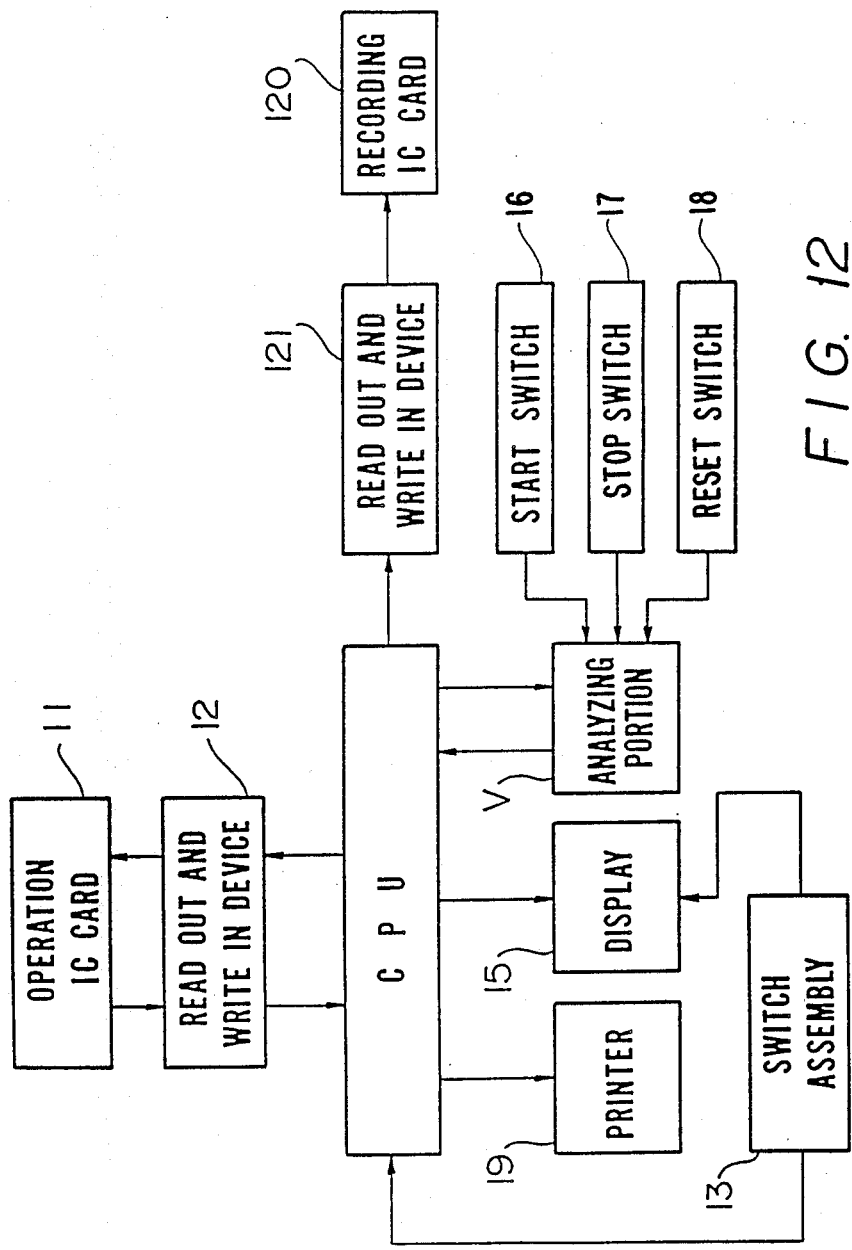
FIG. 12 is a diagram showing a construction of the automatic analyzer.

Another method for arraying the N-type semiconductor 88 and the P-type semiconductor 89 is shown in FIG. 11, in which the pair of an N-type semiconductor 88 and a P-type semiconductor 89 are disposed longitudinally of the center cylindrical part 83a, the chamber sides of the pair of the N-type semiconductor 88 and the P-type semiconductor 89 are connected through the metal 81a, the metals 81b and 81c are connected to the center space sides of the N-type semiconductor 88 and the P-type semiconductor 89 respectively, and a plurality of such sets is arrayed on the center cylindrical part 83a in the circumferential direction thereof and then the sets are connected to a current source, thus obtaining a low-temperature region on the chamber side through an endothermic effect and a high-temperature region on the center space side.

Needless to say, the Peltier effect is reversible by reversing the direction in which the DC current flows, and a similar effect will be obtainable from forming the N-type semiconductor 88 and the P-type semiconductor 89 of an N-type conductor and a P-type conductor, respectively.

The cold thus generated at the junction q is conducted to the chamber 82 from the radiation fins 87, and heat generated at the junction r heats air in the space 83b which is exhausted forcedly outside the cooling device, thereby cooling down the liquid in the reagent containers 9 contained in the chamber 2 efficiently.

The liquid temperature can be set arbitrarily by regulating the voltage of the DC current. Needless to say, heat generated on the junction r can be used, for example, for preliminary heating of the sample.

Because the liquid cooling device is constructed as described, an evaporator, a condenser and a long passage for guiding cold air are not required, unlike a conventional liquid cooling device, and the device can be greatly miniaturized, and cold air can be provided directly at the cells, thus enhancing the cooling efficiency at the same time.

When the reagent container 9 corresponding to the sample to be analyzed arrives at predetermined reagent sucking positions g, h, the reagents are transformed into the reaction cells 1 by the first and second reagent pipettes 4 and 5.

As in the construction of a known pipette device, the first and second reagent pipettes 4 and 5 comprise arms 42, 52 with one end journaled on shafts 41, 51 and pipettes 43, 53 disposed on the other ends of the arms 42, 52, pumps 21, 22 connected to the pipettes 43, 53 for sucking a necessary quantity of the reagent for discharge into the reaction cell 1, each having driving device (not shown) for turning the arms 42, 52 from the reagent sucking positions g, h to the reagent pouring positions b, c and further to the washing positions j, k at a predetermined timing and controlling the lifting at each position.

For measuring the reagent, the suction system is filled with water,, the reagent and water are separated from each other by air during suction and measurement, the reagent only is then discharged, and washing water is put through the inside thereafter to wash the interior of the pipettes 43, 53. When washing, the pipettes 43, 53 are set at the pipette washing positions j, k, and amounts of the sample and material sticking to the outer surfaces of the pipettes 43, 53 are washed off at the positions j, k.

Although not shown, a stirring device is provided on the second reagent pipette 5, moved as the arm 52 is turned, which bubbles the sample in the reaction cell 1 immediately after the second reagent is transferred thereto, and is then washed together with the second reagent pipette 5 at the pipette washing position k.

The optical measuring device 7 forming the detecting unit or observation means is constructed as a diffraction grating system, comprising a light source 70, a plurality of light receiving elements 71 for measuring light irradiated from the light source 70 and passed through the reaction cells 1 and arrayed on a Rowland circle, the aforementioned CPU receiving the output of the elements and converting the quantity of light received on the light receiving element 71 corresponding to a measured material in a reaction cell 1 into voltage and processing the value obtained through analysis, and a memory (not shown) for storing the data. Needless to say, the optical measuring device 7 may be changed into a wave-length conversion system through a filter.

Accordingly, the optical measuring device 7 operates for measuring continuously light passed through all the reaction cells 1 (35 all told in the illustrated embodiment) from the washing position $e_1$ to a measurement finishing position l, thus obtaining a reaction time course of each reaction cell 1.

The washing device 8 washes the interior of each reaction cell 1 for which the optical measuring is finished so that it can be used again by using a known liquid suction motion and a washing water feed motion.

Known readable/writable IC cards are used for the starting IC card 11 for driving and controlling the automatic analyzer A constructed as above and the memory IC card 120 for storing measured data.

Figure 13:
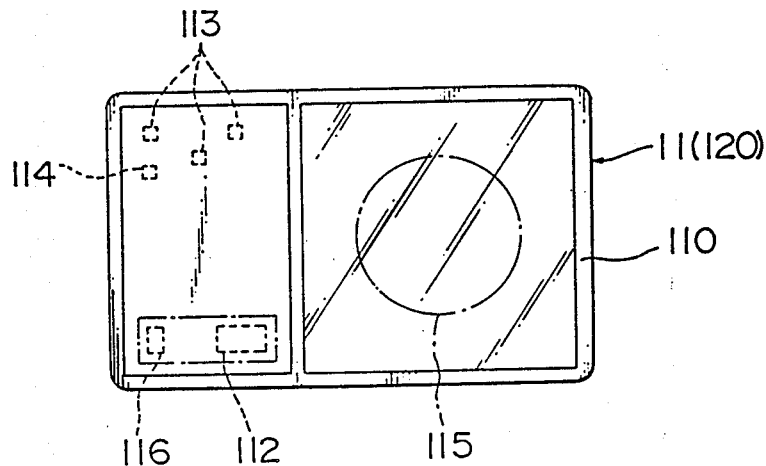
FIG. 13 is an explanatory drawing showing one example of an IC card.

As exemplified in FIG. 13, a data storage 112 on integrated circuit is buried in a card substrate 110, to enable interchanging information with the reader/writer units 12, 121.

That is, the starting IC card 11 and the memory IC card 120 are provided basically with light receiving elements 113 buried in the card substrate 110 for receiving optical signals according to data signals sent from the reader/writer units 12, 121 and transmitting them to the data storage 112, a light emitting element 114 buried in the card substrate 110 for converting data signals generated from the data storage 112 and sending them to the reader/writer units 12, 121, a driving power supply 115 for generating driving voltages for the data storage 112 and the light receiving element 113 buried in the card substrate 110.

The starting IC card 11 and the memory IC card 120 have a CPU constituting the data storage 112 which is not illustrated, an integrated circuit forming a data storage part, a plurality of light receiving elements 113 consisting of a photo transistor for receiving a crystal oscillation signal sent as an optical signal from the reader/writer units 12, 121, a data input signal and a reset signal, a light emitting element 114 consisting of a light emitting diode for converting a data output signal from the integrated circuit into an optical signal and outputting it to the reader/writer units 12, 121, a driving power supply 115 such as a mercury cell or the like arrayed within the card substrate 110 formed of a synthetic resin such as polyester, vinyl chloride or the like at predetermined positions.

Figure 14:
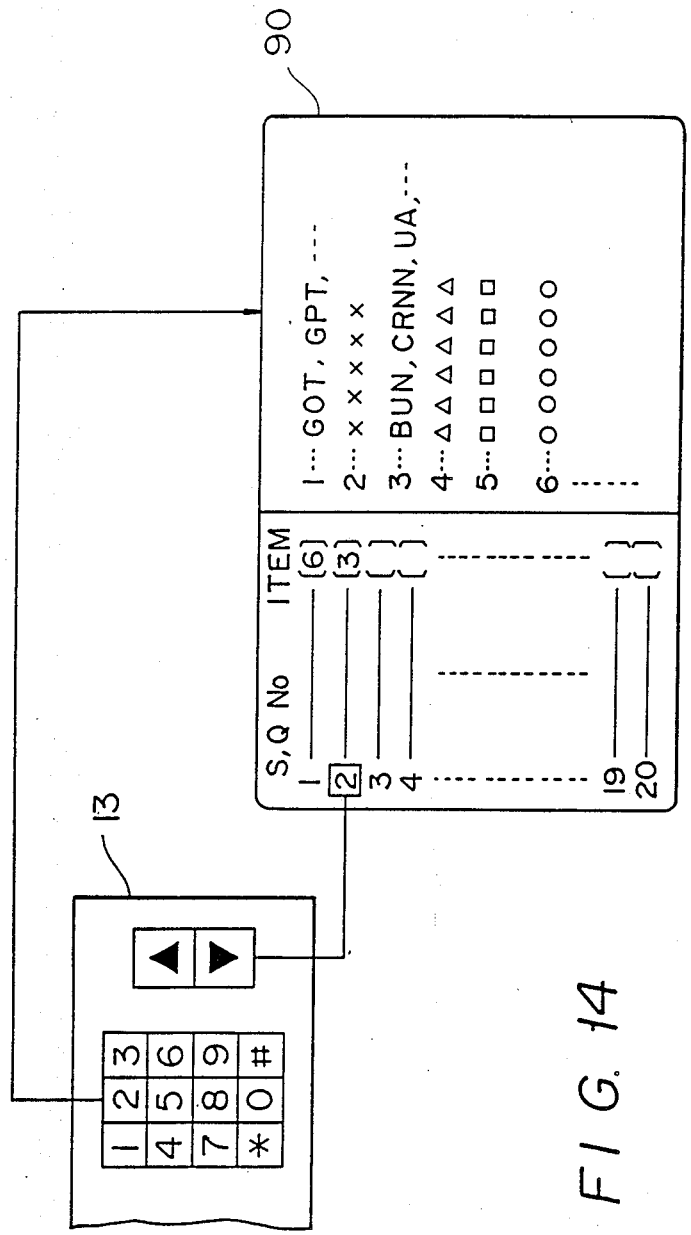
FIG. 14 is an explanatory drawing showing one example of a display on a display unit.

The aforementioned integrated circuit is constituted by an E-EPROM (Electrical Erasable Programmable Read Only Memory) not only readable but also rewritable electrically, wherein a drive controlling means coordinating with a plurality of grouped analysis items is inputted, for example, for six groups as shown in FIG. 14, and also various data such as name, registration no., office, post and other information operators using the automatic analyzer A are inputted.

The analysis items may be grouped by dividing only such items as are necessitated by facilities to install properly into a plurality of groups. However, in consideration of the construction of the automatic analyzer and other factors, it is preferable that the items be grouped by objects of analysis such as hepatic function analysis group such as GOT, GPT and the like, kidney function analysis groups such as BUN, CRNN, UA and the like, or electrolyte analysis groups.

In this case, a particular of the grouped items which can be analyzed by the starting IC card 11 is indicated together with a sequential no. on the left side of a display portion as shown in FIG. 14, of a display unit 90 of the automatic analyzer A, and an analysis group no. and a particular of examination of the analysis group are indicated on the right side of the display portion. The sequential no. refers to a machine serial number of the sample cell 2, and the sequential no. of the sample cells (20 cells in the illustrated embodiment) set on the automatic analyzer A is indicated vertically. The sequential no. will be selected by turning on a suitable switch in the switch group 13. On the other hand, the analysis group no. and the particular of examination of the analysis group indicate which switch of the switch group 13 indicates "what" analysis no., i.e. for example, "1" indicates the hepatic function examination group, "3" indicates the kidney function examination group and so forth.

Accordingly, if the switch "3" of the switch group 13 is turned on for the sample of sequential no. 2, then the selected analysis item no. "3" is indicated by the sequential no. "2" of the display portion.

Then, after selection of the analysis item to all the sequential nos. is over and the ensuing work is completed therefor, a start switch 93 is turned on. When the start switch 93 is turned on, each mechanism of an analyzing portion V operates for carrying out predetermined analyzing work according to the control signal selected by the switch group 13, the analysis data is sent to the CPU, printed out on the printer 19 thereafter, and is inputted to the memory IC card 120 for storage through the reader/writer 121.

Then, operation data read by the reader/writer 121 and the operation procedure of the switch group 13 are inputted in detail to the memory IC card 120, and the construction is such that the stored data cannot normally be retrieved from within the reader/writer 121 disposed in the automatic analyzer A by anyone other than a particular person (maintenance personnel, for example).

The reader/writer units 12, 121 are constructed similarly to a known card reader/writer, which are characterized by a construction comprising a ready access terminal for outputting control signals to the memory IC card 120 and another ready access terminal for inputting and outputting operation data and operation procedure of the switch group 13 to the starting IC card 11, disposing a reader pack, an IC card transmitting/receiving circuit, an arithmetic operation part and a light source in the interior, which are not illustrated.

The reader/writer units 12, 121 constructed as above operate for optically reading operation data inputted to the starting IC card 11 and the memory IC card 120, setting the switch group 13 of the automatic analyzer A to a state ready for use according to the read data, inputting measured data obtained through the optical measuring device 7 and the operation procedure of the switch group 13 to the starting IC card 11 and the memory IC card 120.

The automatic analyzer A of the embodiment is set to on (ready) state only when the starting IC card 11 and the memory IC card 120 are set normally in the reader/writer units 12, 121 respectively, when the subswitch (not shown) which is only an actuating switch of the switch group 13 is off. The subswitch is a switch for setting the switch group 13 to a ready state only when the starting IC card 11 and the memory IC card 120 are set at predetermined positions of the reader/writer units 12, 121, and further when the operation data read by the reader/writer units 12, 121 is determined to be proper, and is inputted to the memory IC card 120 for storage.

The operation of the above-described construction will be described.

First, when the starting IC card 11 with predetermined operation data inputted therein is inserted in the reader/writer 12 through a corresponding card insertion port, the reader/writer 12 irradiates light on a power pack of the starting IC card 11 from the ight source, thereby generating an electromotive force in the card power pack. Thus the starting IC card 11 produces a driving voltage from the electromotive force, and all the circuit parts in the starting IC card 11 are set to a ready state.

Then, starting data stored in the aforementioned storage feeds an oscillation signal generated from an oscillator of the reader/writer 12 to a predetermined light receiving element of the starting IC card 11, and the CPU of the starting IC card 11 is actuated to read out the operation data from the data storage. The data read by the CPU is converted into an optical signal by the predetermined light receiving element and sent to the reader/writer 12. The data sent to the reader/writer 12 is subjected to the necessary data processing in the reader/writer 12, the reader/writer 12 then generates an on actuation signal of the switch group 13 to the subswitch, and the operation data is inputted to the memory IC card 120 set in the reader/writer 121.

On the other hand, when the switch group 13 is set to a ready state by the starting IC card 11, the operator manipulates the switch group 13 to input desired analysis conditions and other such conditions, and the automatic analyzer A operates to carry out predetermined analysis processing according to the inputted operation procedure. However, the operation procedure by the switch group 13 is also inputted automatically in sequence to the memory IC card 120 through the reader/writer 121.

Accordingly, if a fault occurs in the operation of the automatic analyzer A, the maintenance personnel will set the memory IC card 120 extracted from within the reader/writer 121 in a predetermined reader installed in another place, dump the data inputted within the memory IC card 120 to a CRT, printer or the like so that it can be read, thus finding the cause of fault in the operation of the automatic analyzer A easily and quickly.

Next, by actuating the start switch 16, the sample cassette 30 moves each sample cell 2 to the sucking position f, and the operation of sucking the sample is carried out by the sampling pipette 3 at the sample sucking position f. The sampling pipette 3 is turned thereafter and discharges the desired quanity of sample into the reaction cell 1.

When the above operation is over, the reaction cell 1 turns 35 pitches counterclockwise in FIG. 2 and stops, so that each reaction cell 1 is a position one pitch clockwise from its position in the preceding stopped condition in FIG. 2. Thus each reaction cell 1 turns through 35 pitches counterclockwise in FIG. 2 for every discharge of a sample into a cell, i.e. every 20 seconds, and then stops.

When a reaction cell 1 arrives at the first reagent pouring position b on the reaction cell moving device, the reagent table 40 is controlled for rotation synchronously therewith, the reagent cell 9a containing a first reagent corresponding to the characteristic to be measured is moved to the reagent sucking position g, a desired quantity of the first reagent is then sucked up and discharged into the reaction cell 1 which has arrived at the first reagent pouring position b.

After that, the reaction cell 1 is moved to the second reagent pouring/stirring position c, the reagent table 40 is controlled for rotation in concert therewith, the reagent cell 9b containing a second reagent corresponding to the characteristic to be measured is moved to the second reagent sucking position h, a desired quantity of the second reagent is sucked up by the second reagent pipette 5, discharged into the reaction cell 1, and is then bubbled by the stirring device.

Next, the aforementioned reaction cell 1 is moved successively by the reaction cell moving device B, and crosses the light beam of the optical measuring device 7 once during every 35-pitch rotation counterclockwise in FIG. 2, so that optical measurements are carried out over the course of the reaction time in each reaction cell 1.

The reaction cell 1 for which the optical measuring work is completed as described is then moved to the washing device 8, and after a predetermined washing is performed therefor, it is again moved to the sample pouring position a.

The analysis value obtained as described above is subjected to data processing in the CPU, printed out on the printer 19, and is then inputted to the memory IC card 120. If the analysis processing is suspended during the course of being carried out, a stop switch 17 is turned on, and when using the next starting IC card 11, a reset switch 18 is turned on.

In the above-described embodiment, the case where a contactless optical card is used as the IC card is described. However, the invention is not necessarily limited thereto, and an IC card of the contact type, for example, can also be used.

Further, in the embodiment described above, the case where one group is selected from among a plurality of analysis groups by an item switch 14 is described. However, a single item such as GOT, GPT, ZTT or the like may be selected.

Still further, the invention may be constructed so that the automatic analyzer may be controlled and the measuring data may also be stored by an IC card or magnetic card of large capacity instead of inputting operator's information and control signals and storing measuring data all on two IC cards.

INDUSTRIAL APPLICABILITY

As described in detail above, according to the invention, a desired analysis can be selected from an IC card, and an item corresponding to the sample can be selected by operating switches on/off accordingly, and hence the operation is extremely simplified, the system can generally be constructed simply and compactly as well, a simple automatic analyzer which is trouble-free and moderate in cost can thus be provided, and therefore an automatic analyzer complying with requirements of hospitals and clinics can be provided at low cost.

I claim:

1. A multi-item automatic analyzer which comprises:
a reaction cell table holding a plurality of reaction cells;
means for repetitively rotating said table for moving each cell from a sampling position successively through a reagent dispensing position and an optical measuring position to a washing position;
a sampling mechanism at said sampling position for placing a sample to be analyzed into a reaction cell;
a reagent dispensing mechanism at said reagent dispensing position for dispensing a reagent into a reaction cell;
an optical measuring mechanism at said optical measuring position for making optical measurements of samples in the reaction cells passing said optical measuring position;
a washing mechanism at said washing position for washing reaction cells;
a control device connected to said table rotating means, said sampling mechanism, said reagent dispensing mechanism, said optical measuring mechanism and said washing mechanism for operating said means and said mechanisms for carrying out a desired analysis on the respective samples in the respective reaction cells;
an initiating IC card processing means for reading a predetermined analysis operation for a particular sample to be analyzed which has been stored on an initiating IC card which is insertable into said initiating IC card processing means;
a memory IC card processing means for recording data on a memory IC card which is insertable into said memory IC card processing means;
said initiating IC card processing means being connected to said control device for causing said control device to control said table rotating means and said mechanisms to carry out the predetermined analysis and being connected to said memory IC card processing means for recording the predetermined analysis operation on a memory IC card; and
said memory IC card processing means further being connected to said control device and said optical measuring means for recording the actual analysis operation carried out by said analyer and the results of the optical measurements on the same memory IC card.

2. A multi-item automatic analyzer as claimed in claim 1 in which said reagent dispensing mechanism comprises means for holding a plurality of reagent containers and moving said containers along a path to a reagent picking up position, means for picking up a predetermined amount of reagent from a reagent container at said picking up position and dispensing it into a reaction cell, and a constant temperature bath in which said reagent containers are immersed as they move along said path, said constant temperature bath having a heat transfer element along the bottom of the bath, at least two heating elements at intervals along the bottom of said heat transfer element, and temperature control means for controlling the temperature of said heating elements for maintaining the temperature in said bath at a predetermined desired temperature.

3. A multi-item automatic analyzer as claimed in claim 1 in which said table rotating means comprises rotational control means for directing the rotation of said table at each rotation thereof for moving a particular cell from a starting position through a substantially complete rotation of said table to move the particular cell to a position spaced one cell position in the direction opposite the direction of rotation of said table from the starting position, whereby as successive rotations of the table are carried out, the cells progressively move one cell position at a time in a direction opposite the direction of rotation of said table.

* * * * *